United States Patent
Gupta et al.

(10) Patent No.: US 10,379,015 B2
(45) Date of Patent: Aug. 13, 2019

(54) METHOD FOR LABELING CONCENTRATION DENSITY DIFFERENTIALS OF AN ANALYTE IN A BIOLOGICAL SAMPLE

(71) Applicant: Diagnostic BioSystems, Pleasanton, CA (US)

(72) Inventors: Bipin Gupta, Pleasanton, CA (US); Marc Key, Ojai, CA (US)

(73) Assignees: Diagnostic BioSystems, Pleasanton, CA (US); Marc Key, Ojai, CA (US)

(*) Notice: Subject to any disclaimer, the term of this patent is extended or adjusted under 35 U.S.C. 154(b) by 50 days.

(21) Appl. No.: 15/720,239

(22) Filed: Sep. 29, 2017

(65) Prior Publication Data

US 2018/0348099 A1 Dec. 6, 2018

Related U.S. Application Data

(60) Provisional application No. 62/514,926, filed on Jun. 4, 2017.

(51) Int. Cl.
*G01N 1/30* (2006.01)
*G01N 33/53* (2006.01)
(Continued)

(52) U.S. Cl.
CPC ............ *G01N 1/30* (2013.01); *G01N 33/5308* (2013.01); *G01N 33/581* (2013.01);
(Continued)

(58) Field of Classification Search
None
See application file for complete search history.

(56) References Cited

U.S. PATENT DOCUMENTS

| 5,242,817 A | 9/1993 | Kelly et al. |
| 8,658,361 B2 * | 2/2014 | Wu ..................... C12Q 1/6818 435/6.1 |

(Continued)

FOREIGN PATENT DOCUMENTS

WO   WO-2011133625 A1 * 10/2011 ........... C12Q 1/6841

OTHER PUBLICATIONS

Laakso, M; Tanner, M; Isola, J; "Dual-colour chromogenic in situ hybridization for testing of HER-2 oncogene amplification in archival breast tumours" Journal of Pathology, 210, 3-9, 2006 (Year: 2006).*

(Continued)

*Primary Examiner* — David W Berke-Schlessel
(74) *Attorney, Agent, or Firm* — Patentfile, LLC; Bradley C. Fach; Steven R. Kick

(57) ABSTRACT

A method for labeling concentration density differentials of an analyte in a biological sample is provided. The method may including the steps of: binding an enzyme to an analyte contained in a sample, the enzyme capable of acting on at least two chromogens; incubating the sample with a first chromogen for a first time period to generate a first color chromogen-enzyme product, the first color chromogen-enzyme product reflecting light observable as a first color; and incubating the sample with a second chromogen for a second time period to generate a second color chromogen-enzyme product, the second color chromogen-enzyme product reflecting light observable as second color. A combination of the light observable as the first color and the light observable as the second color may be observable as a third color, and each color may describe a different analyte density in the biological sample.

20 Claims, 3 Drawing Sheets

(51) Int. Cl.
*G01N 33/68* (2006.01)
*G01N 33/58* (2006.01)

(52) U.S. Cl.
CPC ... *G01N 33/6803* (2013.01); *G01N 2001/302* (2013.01); *G01N 2333/908* (2013.01); *G01N 2333/916* (2013.01)

(56) References Cited

U.S. PATENT DOCUMENTS

| | | | |
|---|---|---|---|
| 2006/0040341 A1 | 2/2006 | Bland et al. | |
| 2012/0028298 A1 | 2/2012 | Takayama et al. | |
| 2013/0189730 A1 | 7/2013 | Freeland et al. | |
| 2013/0260379 A1* | 10/2013 | Alexander | G01N 33/542 435/6.11 |
| 2014/0017749 A1 | 1/2014 | Deinhammer et al. | |
| 2014/0051118 A1 | 2/2014 | Matthiesen et al. | |
| 2015/0216664 A1 | 8/2015 | Ingham et al. | |
| 2017/0175178 A1* | 6/2017 | Lohse | C07D 311/82 |
| 2017/0183740 A1 | 6/2017 | Yu et al. | |
| 2018/0147166 A1 | 5/2018 | Dong et al. | |

OTHER PUBLICATIONS

NPL—Cite No. 1—Van der Loos et al. An Immunoenzyme Triple-Staining Method Using Both Polyclonal and Monoclonal Antibodies from the Same Species. Application of Combined Direct, Indirect, and Avidin-Biotin Complex (ABC) Technique. Journal of Histochemistry and Cytochemistrry (1987), v35(11), p. 1199-1204. (Year:1987).

NPL—Cite No. 2—Van der Loos Chromogens in Multiple Immunohistochemical Staining Used for Visual Assessment and Spectral Imaging: The Colorful Future. The J Histotchnol (2010), v33(1), v31-40. (Year: 2010).

NPL—Cite No. 3—Lauter et al. Two-color flourescent in situ hybridization in the embryonic zebrafish brain using differential detection systems. Developmental Biology (2011), v11(43), 11 pages. (Year:2011).

* cited by examiner

METHOD FOR LABELING CONCENTRATION DENSITY DIFFERENTIALS OF AN ANALYTE IN A BIOLOGICAL SAMPLE

CROSS REFERENCE TO RELATED APPLICATIONS

This application claims priority to and the benefit of the filing date of U.S. Provisional Application No. 62/514,926, filed on Jun. 4, 2017, entitled "Density Measurement Of Target Analytes In Biological Samples", which is hereby incorporated by reference in its entirety.

FIELD OF THE INVENTION

This patent specification relates to the field of analyte density measurements. More specifically, this patent specification relates to methods for density measurement of target analytes in biological samples by differential staining.

BACKGROUND

Biological samples of cells and/or tissues are obtained for purposes of analyzing the biological constituents that comprise the sample. The analysis may be a molecular analysis to determine if a particular analyte, such as an enzyme, protein, or nucleic acid, is present within the sample. The presence or absence of an analyte is frequently used to determine a disease state, such as cancer.

Prior to the analysis the biological sample must be prepared by appropriate methods, such as fixation, embedding, and sectioning. For example, a tissue biopsy may be removed from a patient and processed to adhere the tissue section or biological sample to a microscope slide. The biological sample is then stained in a manner to produce a colored stain on the tissue that corresponds to the analyte under evaluation. It is typical that the analyte will be located within various cells or structures distributed throughout the tissue. However the analyte density may vary greatly by location. In some instances it is desirable to know the analyte density level at the various locations.

Two common staining methods are in situ hybridization (ISH) for evaluation of nucleic acid analytes and immunohistochemistry (IHC) for evaluation of antigen analytes, such as proteins. In these methods a single chromogen is used to stain the sample. Sites of high analyte density will show a darker reaction and sites of low analyte density will show a weaker reaction. However, there is only a single color, light or dark, generated. Unfortunately, the analyte density in the sample is not easily evaluated by direct observation of laboratory personnel because only a single color is generated, and the human eye cannot distinguish between shades of color as easily as it can distinguish between different colors. Therefore, current methods of determining analyte density in a sample require the use of an image analysis system which records a digital image of the stained sample. The digital image is then converted to gray scale and the pixel density is measured from 0-255. Since gray-scale measurements typically use a range of 0-255, measurements of analyte density are limited to being described by this scale.

Therefore a need exists for novel methods for density measurement of target analytes in biological samples by differential staining. A further need exists for novel methods for density measurement of target analytes in biological samples which are easily evaluated by direct observation of laboratory personnel. There is also a need for novel methods for density measurement of target analytes in biological samples which do not require the use of an image analysis system. Furthermore, a need exists for novel methods for density measurement of target analytes in biological samples which do not limit descriptions of the analyte density to a scale of 0-255.

BRIEF SUMMARY OF THE INVENTION

A method for labeling concentration density differentials of an analyte in a biological sample is provided in which the analyte under investigation is stained two or more different colors depending on the density of the analyte within the tissue. This method allows the investigator to view the different colors under the microscope and to quantify analyte density levels without the use of an image analysis system. While differential staining techniques exist, they are directed to staining different analytes different colors. For example, Gram staining uses two dyes: Crystal violet and Fuchsin or Safranin (the counterstain) to differentiate between Gram-positive bacteria (large Peptidoglycan layer on outer surface of cell) and Gram-negative bacteria. The expected results from using two different chromogens to stain a single analyte is that the two stains would obscure each other which is why using two different chromogens is commonly discouraged. The novel method for labeling concentration density differentials of an analyte in a biological sample is a useful and easy method to estimate analyte density in a tissue in which the distribution of the first, second, and third colors over the tissue is directly proportional to analyte density in the tissue.

In some embodiments, a method for labeling concentration density differentials of an analyte in a biological sample may including the steps of: binding an enzyme to an analyte contained in a sample, the enzyme capable of acting on at least two chromogens; incubating the sample with a first chromogen for a first time period to generate a first color chromogen-enzyme product, the first color chromogen-enzyme product reflecting light observable as a first color; and incubating the sample with a second chromogen for a second time period to generate a second color chromogen-enzyme product, the second color chromogen-enzyme product reflecting light observable as second color. A combination of the light observable as the first color and the light observable as the second color may be observable as a third color, and each color may describe a different analyte density in the biological sample.

In further embodiments, a method for labeling concentration density differentials of an analyte in a biological sample may including the steps of: binding an enzyme to an analyte contained in a sample, the enzyme capable of acting on at least two chromogens; incubating the sample with a first chromogen for a first time period to generate a first color chromogen-enzyme product that is accumulated in the biological sample at the binding site of the analyte, the first color chromogen-enzyme product observable as a first color; and incubating the sample with a second chromogen for a second time period to generate a second color chromogen-enzyme product that is accumulated in the biological sample at the binding site of the analyte, the second color chromogen-enzyme product observable as a second color. A combination of the first color chromogen-enzyme product and second color chromogen-enzyme product may be observable as a third color, and the first color may describe a first analyte density, the second color may describe a second analyte density, and the third color may describe a third analyte density.

In still further embodiments, the second analyte density may be greater than the first analyte density, and the second analyte density may be greater than the third analyte density.

In yet still further embodiments, the third analyte density may be less than the second analyte density, and the second analyte density may be greater than the first analyte density.

It is an object of the invention to provide a method of density measurement of a target analyte in a biological sample and to visually distinguish analyte density levels by differential staining.

It is another object of the invention to provide a method of density measurement of a target analyte in a biological sample that are comprised of cells and/or tissues.

It is a further object of the invention to provide a method of density measurement of a target analyte in a biological sample that are analyzed by immunohistochemistry.

It is another object of the invention to provide a method of density measurement of a target analyte in a biological sample that are analyzed by in situ hybridization.

It is a further object of the invention to provide a method of density measurement of a target analyte in a biological sample that distinguishes between density levels by staining each level with a different color, where each color can be visualized microscopically.

BRIEF DESCRIPTION OF THE DRAWINGS

Some embodiments of the present invention are illustrated as an example and are not limited by the figures of the accompanying drawings, in which like references may indicate similar elements and in which.

DETAILED DESCRIPTION OF THE INVENTION

Figure 1:
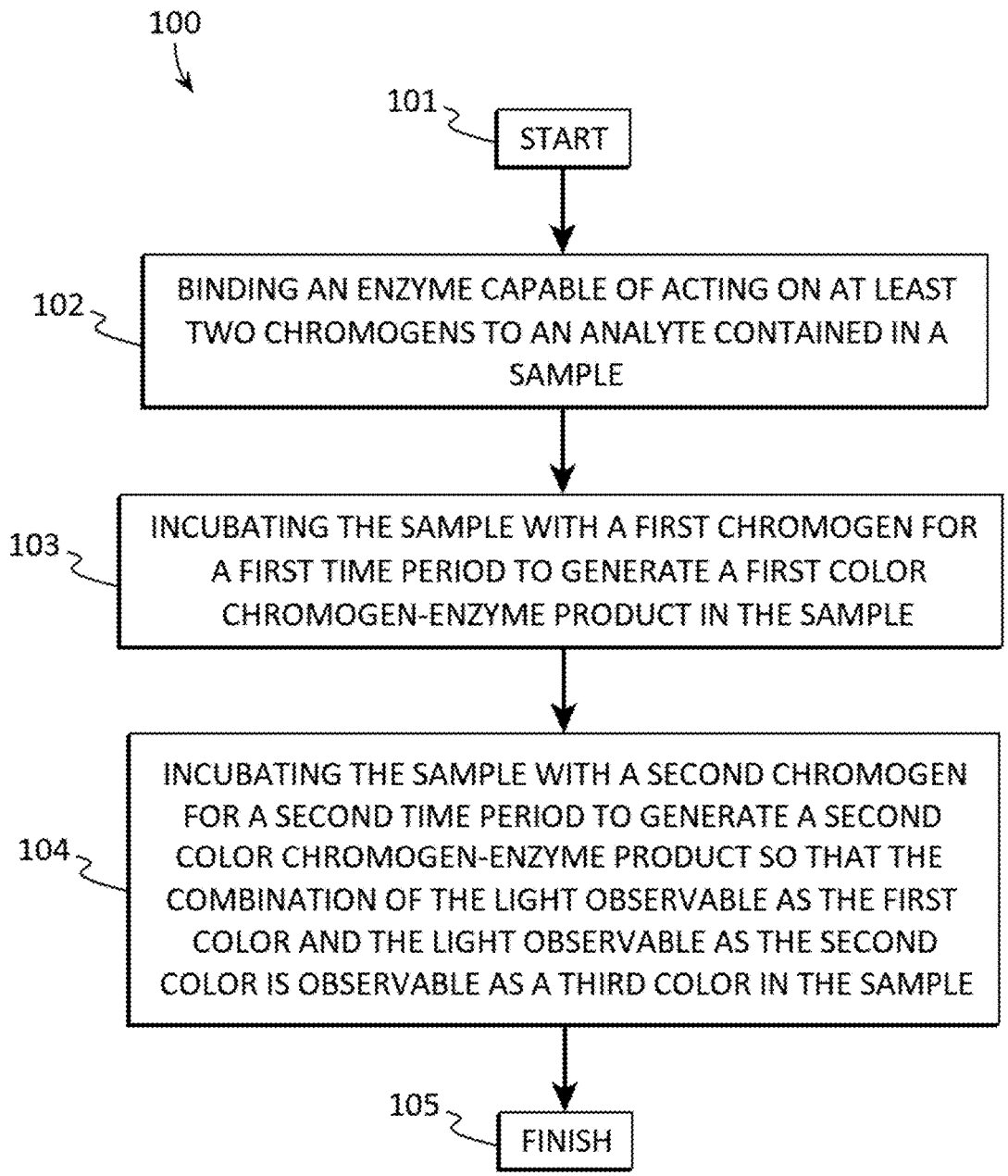
FIG. 1 depicts a block diagram of an example of a method for labeling concentration density differentials of an analyte in a biological sample according to various embodiments described herein.
Figure 2:
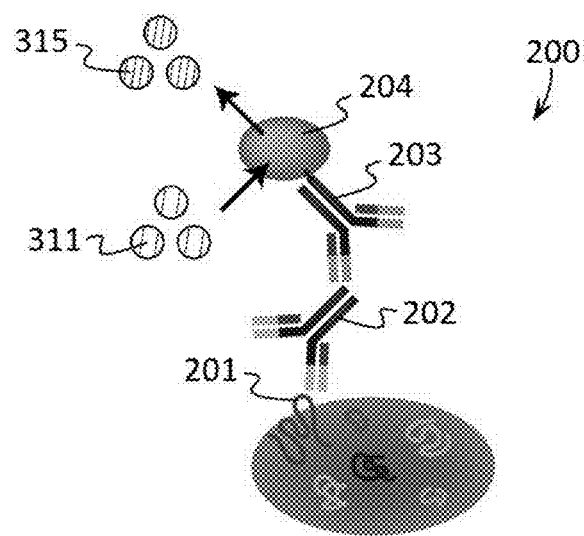
FIG. 2 illustrates a diagram of an example of an analyte in a biological sample being labeled with a first color chromogen-enzyme product using a first chromogen according to various embodiments described herein.
Figure 3:
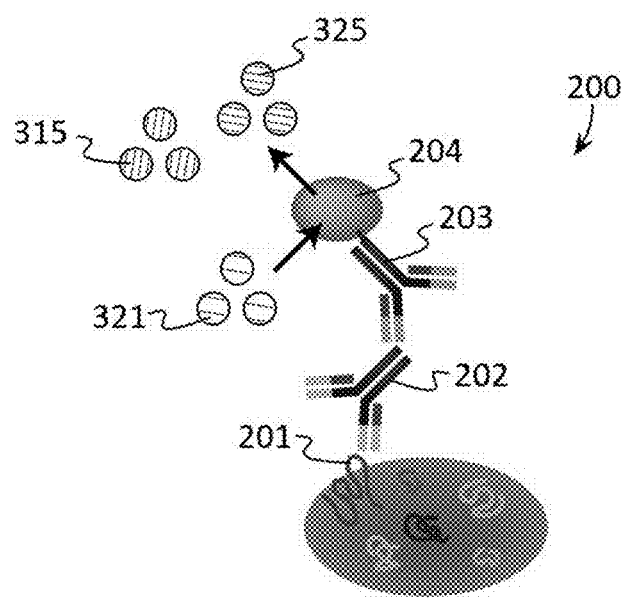
FIG. 3 shows a diagram of an example of an analyte labeled with a first color chromogen-enzyme product in a biological sample being labeled with a second color chromogen-enzyme product using a second chromogen according to various embodiments described herein.
Figure 4:
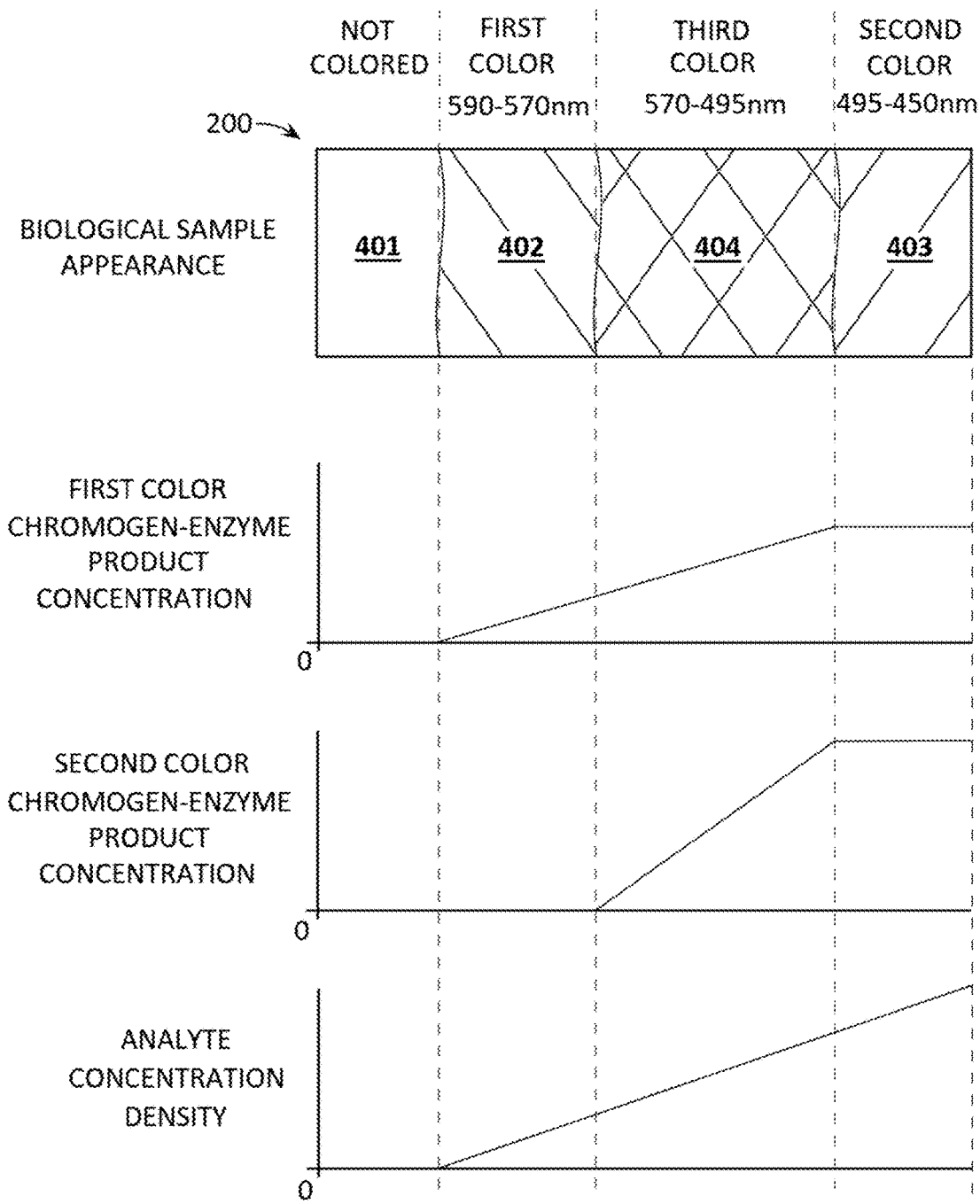
FIG. 4 depicts a schematic of an example of a sample having an analyte labeled with two different color chromogen-enzyme products to label concentration density differentials of the analyte according to various embodiments described herein.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

The specific examples and processes illustrated in the attached drawings, and described in the following specification, are simply exemplary embodiments of the inventive concepts defined in the appended claims. Hence, specific appearances and other physical characteristics relating to the embodiments disclosed herein are not to be considered as limiting, unless the claims expressly state otherwise.

Although the terms "first", "second", etc. are used herein to describe various elements, these elements should not be limited by these terms. These terms are only used to distinguish one element from another element. For example, the first element may be designated as the second element, and the second element may be likewise designated as the first element without departing from the scope of the invention.

As used in this application, the term "about" or "approximately" refers to a range of values within plus or minus 10% of the specified number. Additionally, as used in this application, the term "substantially" means that the actual value is within about 10% of the actual desired value, particularly within about 5% of the actual desired value and especially within about 1% of the actual desired value of any variable, element or limit set forth herein.

New methods for density measurement of target analytes in biological samples by differential staining are discussed herein as referenced in FIGS. 1-4. In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention, and is not intended to limit the invention to the specific embodiments illustrated by the figures or description below.

Biological samples 200 of cells and/or tissues may be obtained for purposes of analyzing one or more analytes 201 or biological constituents that comprise the sample 200. In some embodiments, sample analysis may be performed by methods of immunohistochemistry for analyzing protein components, or in situ hybridization for analyzing nucleic acid components, such as a sequence of deoxyribonucleic acid (DNA) nucleotides or a sequence of ribonucleic acid (RNA) nucleotides. Prior to the analysis, the sample 200 must be prepared by appropriate methods. For example, a tissue biopsy is removed from a patient and processed by the following steps:

1. Fixation: Tissue is fixed to stop all metabolic activity and to preserve the molecular structure of the tissue.
2. Embedding: The tissue is embedded in solid paraffin to provide a firm surrounding matrix.
3. Sectioning: The solid paraffin containing the tissue is cut into thin sections of approximately 4 u, and each section is adhered to a microscope slide.

The microscope slide with the adherent tissue section may then be prepared for staining. First the paraffin is removed, then the tissue is rehydrated in an aqueous buffer, and finally the tissue is chemically treated to recover analytes and render them accessible for detection in a process called target retrieval, or more specifically in the case of immunohistochemistry call antigen retrieval.

Biological samples 200 containing cells or tissues are fixed to render them metabolically inactive and preserve molecular structures. A common fixative for this purpose includes solutions of formalin in aqueous solutions. In addition to formalin there are several fixative methods that can be used, such as alcohols, (methanol and ethanol), acetone, glutaraldehyde, and combinations thereof.

Embedding is the process of infiltrating paraffin into, and around, the biological sample. First the water is removed by dehydration, for example in alcohol, next the alcohol is removed and replaced with a solvent that is miscible with paraffin, such as xylene, toluene, or other hydrocarbon solvent. The tissue thus prepared is then infiltrated with melted paraffin at a temperature of around 60 C, or at a temperature sufficient to keep the paraffin in a melted state. After infiltration the biological samples are cooled, and the paraffin solidifies to create a solid matrix surrounding the sample. There are also embedding methods that do not include paraffin. One such method is to freeze the tissue sample into a solid block of ice. This renders the sample sufficiently rigid that it can be sectioned into thin slices using a cryostat instrument. Tissues prepared in this manner avoid the paraffin-embedding process as well as the deparaffinization and rehydration processes.

The sample 200 can now be easily cut into thin sections by using a microtome or similar cutting device. The thin paraffin sections, containing the tissue, are usually cut with a thickness of about 4 u. Each section may then be placed upon a microscope slide where it will attach by means of electrostatic charges between the tissue section and the slide.

The slides of the sample 200, thus prepared and containing paraffin, are further processed to remove the paraffin in a process called deparaffinization. Slides for deparaffinization are treated with a paraffin solvent, such as xylene, toluene, or similar hydrocarbon solvent, and the paraffin is dissolved. The next step involves removing the paraffin solvent, and replacing it with alcohol. Because alcohol is miscible with water the slides can now be placed into an aqueous buffer bath for rehydration.

After rehydration the slides with the attached tissue samples 200 are subjected to target retrieval which may be a physical or chemical treatment to release the analytes 201 and make them accessible for subsequent staining. Target retrieval may be performed in various different ways. Typically the rehydrated microscope slides, containing tissues, are submerged into a chemical solution and the subjected to heat at about 100 C. This process of heat-induced target retrieval is designed to render the target molecules susceptible to staining methods. In some instances it is possible to retrieve targets by using enzymatic methods rather than chemical and physical methods. In this method the microscope slides containing the sample are exposed to proteolytic enzymes which act to partially digest the tissue and render the analytes accessible to staining. Such proteolytic enzymes may include pepsin, trypsin, proteinase K, protease XXIV, chymotrypsin, and ficin as some examples.

Once prepared the samples 200 are ready for staining. There are two methods in common use for staining that are In Situ Hybridization and Immunohistochemistry, which will be further described below.

In Situ Hybridization (ISH).

In the ISH method the target analyte 201 is a nucleic acid usually either an RNA nucleotide sequence or DNA nucleotide sequence target. In the first step the sample is contacted with a probe 202 that will specifically recognize and bind to its target analyte 201. Probes 202 are small lengths or strands of nucleic acid sequences that have been engineered to contain a series of bases that are complementary to the base sequence of the target analyte 201. Since complementary strands of nucleic acids will pair together, the probe 202 will specifically bind to its complementary target nucleic acid. As an example an investigator may wish to determine whether a particular gene (target analyte 201) is present or absent in a sample. If the gene sequence of the target analyte 201 is known, it is then possible to construct a probe with a complementary nucleic acid sequence. If the target analyte 201 is present, then the probe will bind to the target. If the target analyte 201 is absent then no binding will occur. The next step is to detect whether or not a binding event has occurred. Typically the probe will be produced to include a detectable marker 204. For example this detectable marker 204 could be an enzyme. If a binding event has occurred then the enzyme will be present at the binding site. If no binding event has occurred then the enzyme will not be present. In one example the enzyme could be Horseradish Peroxidase (HRP), although other enzymes can be used.

Next the presence or absence of the HRP enzyme is evaluated. The HRP enzyme reacts with various chromogenic compounds (chromogens) to produce a colored-reaction product. The colored-reaction product then stains the tissue at the site of HRP binding. When the tissue is viewed microscopically the colored reaction product can be observed. The presence of the colored reaction product indicates that the target analyte 201 was present, whereas no colored reaction product indicates that the target analyte 201 was absent.

Immunohistochemistry (IHC)

In the IHC method, the target analyte 201 is called an antigen, and it is most generally used to stain protein targets, although other organic molecules such as carbohydrates and lipids can also be stained. The term immunohistochemistry technically refers to the staining of tissues using antibodies. However, for purposes of this invention we are also including isolated cells in this definition. As an example an investigator may wish to analyze a tissue for the presence or absence of a particular protein. First a tissue suspected of containing a target analyte 201 is exposed to an antibody that has been produced to specifically bind with the target. After the antibody is applied a binding event will occur if the target protein is present, but no binding will take place if the target protein is absent. The next step is to determine if a binding event has occurred. Prior to use the antibody is labeled with a detectable marker 204. The detectable marker 204 may be another antigen, small molecule, or enzyme. In the simplest instance the detectable marker 204 is an enzyme (enzyme marker 204). If the binding has occurred then enzyme will be present at the binding site, otherwise no enzyme is present. Finally the present or absence of enzyme marker 204 is determined by application of a chromogen. Typically, chromogens are a mixture of two different compounds. For example, first compound may be H2O2, which is also known as the substrate, and the second compound is the chromogen. Together these are commonly called the substrate/chromogen to indicate that they are a mixture of two compounds. The substrate/chromogen may react with the enzyme marker 204 and is converted from a colorless chromogen to a colored chromogen that stains the area of the binding site.

The above examples of ISH and IHC represent methods of staining of an analyte that is well known and is commonly used for this purpose. There are other variations of these methods that could also be employed and would still be compatible with the present invention. Instead of an enzyme the probe or antibody could be labeled with another marker 204 such as an antigen or small molecule. These labels are not directly visualized but are next linked by one or more intermediate steps to an enzyme. Such methods are called indirect methods. However ultimately the binding site, through one or more intermediate steps, becomes labeled with an enzyme.

The enzyme marker 204 may be chosen from any enzyme which is known to react with a colorless chromogen/substrate to create a colored chromogen capable of staining the tissue. The two most common enzyme markers 204 for this purpose are Horseradish Peroxidase (HRP) and Alkaline Phosphatase (AP). Both HRP and AP have been used successfully in ISH and IHC procedures. Multiple different chromogens (chromogen/substrates) are available for both enzymes that can yield multiple different colors.

The present invention will now be described by example and through referencing the appended figures representing preferred and alternative embodiments. FIG. 1 depicts a block diagram of an example of a method for labeling concentration density differentials of an analyte in a biological sample ("the method") 100 according to various embodiments described herein. The method 100 may be used by an individual to not only easily determine the presence or absence of an analyte 201 but also the density of the analyte 201. The method 100 is a novel process of chromogen layering where a first chromogen 311 and a first color stain is produced on the sample 200. This is followed by a second chromogen 321 and a second color stain is produced. By overlaying the second stain on top of the first stain a unique third color is produced. The distribution of these three colors throughout the sample 200 is proportional to analyte 201 density so that each color describes a different analyte 201 density in the biological sample 200. Prior to the beginning the method 100 the sample 200 may be prepared by appropriate methods. For example, a tissue biopsy is removed from a patient and processed by fixation, embedding, sectioning, and target or antigen retrieval.

The method 100 may begin 101, and an enzyme marker 204 capable of acting on at least two chromogens may be bound to an analyte 201 contained in the biological sample 200 in step 102. For example, a tissue biopsy is obtained from a patient suspected of having a carcinoma and a biological sample 200 is prepared from the biopsy. The presence or absence of cytokeratin protein in the sample 200 is important for distinguishing between carcinomas of epithelial origin (cytokeratin positive) and other types of tumors such as lymphoma or melanoma (cytokeratin negative). The analyte 201 may be cytokeratin, and step 102 may be accomplished by incubating the biological sample 200 with a target antibody 202 for cytokeratin for 20 minutes, rinsing, incubating the sample 200 with linker antibody 203 labeled with Horseradish Peroxidase (HRP) for 20 minutes, and then rinsing. The enzyme marker 204 may be capable of acting on at least two chromogens. In some embodiments, the enzyme of the enzyme marker 204 may comprise Horseradish Peroxidase. In other embodiments, the enzyme of the enzyme marker 204 may comprise Alkaline Phosphatase. In alternative embodiments, the enzyme of the enzyme marker 204 may comprise any other peroxidases, any other phosphatase, beta-galactosidase, or any enzyme that reacts with a colorless compound to create a colored chromogen capable of staining the biological specimen.

In some embodiments, the target analyte 201 may be a nucleic acid usually either an RNA nucleotide sequence or DNA nucleotide sequence target and ISH method for binding an enzyme to the analyte 201 may be used. The sample 200 may be contacted with a probe that will specifically recognize and bind to its nucleic acid (nucleotide sequence) target. Probes are small lengths of nucleic acids that have been engineered to contain a series or sequence of bases that are complementary to the base sequence of the target analyte 201. Since complementary strands of nucleic acids will pair together, the probe will specifically bind to its complementary target nucleic acid. If the target analyte 201 is present, then the probe will bind to the target. If the target analyte 201 is absent then no binding will occur. The probe may be produced to include a detectable marker, such as an enzyme. If a binding event has occurred then the enzyme will be present at the binding site. If no binding event has occurred then the enzyme will not be present. In further embodiments, the analyte 201 may be a nucleotide sequence (RNA nucleotide sequence or DNA nucleotide sequence) of a nucleic acid used in the synthesis of a protein such as Human Epidermal Growth Factor Receptor-2 (HER2/neu), Programmed death-ligand 1, Anaplastic lymphoma kinase, epidermal growth factor receptor (EGFR), Receptor tyrosine-protein kinase, cytokeratin protein, and Mast/stem cell growth factor receptor, while in still further embodiments, the analyte 201 may be any other nucleic acid or nucleic acid sequence.

In other embodiments, the target analyte 201 may be a protein contained in the biological sample 200. The biological sample 200 may be exposed to an antibody that has been produced to specifically bind with the target protein. After the antibody is applied a binding event will occur if the target protein is present, but no binding will take place if the target protein is absent. Prior to use the antibody is labeled with a detectable marker. The detectable marker 204 may be another antigen, small molecule, or enzyme. In the simplest instance the detectable marker 204 is an enzyme. If the binding has occurred then enzyme marker 204 will be present at the binding site, otherwise no enzyme is present. In further embodiments, the analyte 201 may be a protein such as Human Epidermal Growth Factor Receptor-2 (HER2/neu), Programmed death-ligand 1, Anaplastic lymphoma kinase, epidermal growth factor receptor (EGFR), Receptor tyrosine-protein kinase, cytokeratin protein, and Mast/stem cell growth factor receptor, while in still further embodiments, the analyte 201 may be any other protein.

Next, the sample 200 may be incubated with a first chromogen 311 (substrate/chromogen) for a first time period to generate a first color chromogen-enzyme product 315 in step 103. The enzyme marker 204 bound to the analyte 201 may react with the first chromogen 311 to produce a first color chromogen-enzyme product 315 which may reflect light observable as a first color.

In some embodiments, the first chromogen 311 may comprise Diaminobenzidine (DAB), Aminoethylcarbazole (AEC), tetramethylbenzidine (TMB), 4-Chloronaphthol (4CN)), 4CN+p-phenylenediamine, Benzidine, or Phenylenediamine, Naphthol Phosphate plus Fast Red, Naphthol Phosphate plus Fast Blue, Bromo chloro indoxyl phosphate (BCIP), and Chloro indoxyl phosphate (CIP), while in other embodiments, the first chromogen 311 may comprise any other chromogen which may be acted upon by the enzyme marker 204 of step 102. In further embodiments of the method 100, the of the enzyme marker 204 may be Horseradish Peroxidase, and the first chromogen 311 may comprise Diaminobenzidine (DAB), Aminoethylcarbazole (AEC), tetramethylbenzidine (TMB), 4-Chloronaphthol (4CN)), 4CN+p-phenylenediamine, Benzidine, or Phenylenediamine. In still further embodiments of the method 100, the enzyme of the enzyme marker 204 may be Alkaline Phosphatase, and the first chromogen 311 may comprise Naphthol Phosphate plus Fast Red, Naphthol Phosphate plus Fast Blue, Bromo chloro indoxyl phosphate (BCIP), or Chloro indoxyl phosphate (CIP).

Preferably, the first color chromogen-enzyme product 315 may be a precipitating dye which binds to the tissue at the sites in the sample 200 where it is deposited, namely at the site of the enzyme marker 204 bound to the analyte 201. Once bound the first color chromogen-enzyme product 315 remains insoluble and is not washed off by subsequent processing steps, such as water and buffer solutions. In some embodiments, the first color chromogen-enzyme product 315 may be observable as a first color in the sample 200. In further embodiments, the first color chromogen-enzyme product 315 may reflect light which may be observable as a first color in the sample 200.

Continuing the above cytokeratin example, the first chromogen 311 may be HRP-Yellow, and the sample 200 may be incubated with the HRP-Yellow for five minutes to generate a first color chromogen-enzyme product 315 having a first color of yellow or reflecting light observable as the color yellow deposited on the biological sample 200 if cytokeratin is present and the sample 200 may be rinsed.

Next, the sample 200 may be incubated with a second chromogen 321 (substrate/chromogen) for a second time period to generate a second color chromogen-enzyme product 325 which may reflect light observable as a second color in step 104. The enzyme marker 204 bound to the analyte 201 may react with the second chromogen 321 to produce a second color chromogen-enzyme product 325. The second chromogen 321 may be any chromogen other than the chromogen used as the first chromogen 311. In some embodiments, the first color chromogen-enzyme product 315 may be observable as the color yellow (commonly recognized as light observable with a wavelength of approximately 570-590 nm), the second color chromogen-enzyme product 325 may be observable as the color blue (commonly recognized as light observable with a wavelength of approximately 450-495 nm), and the third color may be observable as the color green (commonly recognized as light observable with a wavelength of approximately 495-570 nm). In further embodiments, the first color chromogen-enzyme product 315 may be observable as the color red (commonly recognized as light observable with a wavelength of approximately 620-750 nm), the second color chromogen-enzyme product 325 may be observable as the color blue (commonly recognized as light observable with a wavelength of approximately 450-495 nm), and the third color may be observable as the color purple or violet (commonly recognized as light observable with a wavelength of approximately 380-450 nm). In still further embodiments, the first color chromogen-enzyme product 315 may be observable as the color yellow (commonly recognized as light observable with a wavelength of approximately 570-590 nm), the second color chromogen-enzyme product 325 may be observable as the color red (commonly recognized as light observable with a wavelength of approximately 620-750 nm), and the third color may be observable as the color orange (commonly recognized as light observable with a wavelength of approximately 590-620 nm).

In some embodiments, the second chromogen 321 may comprise Diaminobenzidine (DAB), Aminoethylcarbazole (AEC), tetramethylbenzidine (TMB), 4-Chloronaphthol (4CN)), 4CN+p-phenylenediamine, Benzidine, Phenylenediamine, Naphthol Phosphate plus Fast Red, Naphthol Phosphate plus Fast Blue, Bromo chloro indoxyl phosphate (BCIP), and Chloro indoxyl phosphate (CIP), while in other embodiments, the second chromogen 321 may comprise any other chromogen, other than the first chromogen 311, which may be acted upon by the enzyme marker 204 of step 102. In further embodiments of the method 100, the enzyme of the enzyme marker 204 may be Horseradish Peroxidase, and the second chromogen 321 may comprise Diaminobenzidine (DAB), Aminoethylcarbazole (AEC), tetramethylbenzidine (TMB), 4-Chloronaphthol (4CN)), 4CN+p-phenylenediamine, Benzidine, or Phenylenediamine. In still further embodiments of the method 100, the enzyme of the enzyme marker 204 may be Alkaline Phosphatase, and the second chromogen 321 may comprise Naphthol Phosphate plus Fast Red, Naphthol Phosphate plus Fast Blue, Bromo chloro indoxyl phosphate (BCIP), or Chloro indoxyl phosphate (CIP).

Preferably, the second color chromogen-enzyme product 325 may be a precipitating dye which binds to the tissue at the sites in the sample 200 where it is deposited, namely at the site of the enzyme marker 204 bound to the analyte 201. Once bound the second color chromogen-enzyme product 325 remains insoluble and is not washed off by subsequent processing steps, such as water and buffer solutions. In some embodiments, the second color chromogen-enzyme product 325 may be observable as a second color in the sample 200. In further embodiments, the second color chromogen-enzyme product 325 may reflect light which may be observable as a second color in the sample 200.

Continuing the above cytokeratin example, the second chromogen 321 may be HRP-Blue, and the sample 200 may be incubated with the HRP-Blue for five minutes to generate a second color chromogen-enzyme product 325 having a second color of blue or reflecting light observable as the color blue deposited on the biological sample 200 if cytokeratin is present and the sample 200 may be rinsed. In some embodiments, a combination of the light observable as the first color and the light observable as the second color may be observable as a third color, and each color may describe a different analyte 201 density in the biological sample 200. In further embodiments, the analyte 201 density described by the second color may be greater than the analyte 201 density described by the first color, and the analyte 201 density described by the second color may be greater than the analyte 201 density described by the third color. In still further embodiments, the analyte 201 density described by the third color may be less than the analyte 201 density described by the second color, and the analyte 201 density described by the second color may be greater than the analyte 201 density described by the first color.

After step 104, the method 100 may finish 105, and the biological sample 200 may be observed, such as through a microscope, digital or non-digital photograph, or as an image on a digital display, to determine if the analyte 201 is present in the sample 200 and to determine the concentration density differentials of an analyte 201 in the biological sample 200. If the analyte 201 is present in the sample 200, at least one color chromogen-enzyme product may be present in the sample 200. In some embodiments, the color chromogen-enzyme product may reflect light observable as a first color. In further embodiments, the color chromogen-enzyme product may be observable as a first color. The concentration differentials of the analyte 201 in the biological sample 200 may be determined by observing the number of color chromogen-enzyme products and their intensity.

After completion of the method 100, the stained sample 200s, preferably mounted on microscope slides, may be viewed under a microscope or any other suitable method by a trained individual such as a microscopist. The microscopist may view the slides and note the color pattern of staining. In certain areas of the slide where analyte 201 density is sparse a first staining color will be observed. In areas of the tissue where analyte 201 density is heavy a second color will be observed. Where analyte 201 density is intermediate between sparse and medium or between medium and dense, an intermediate color will be observed so that in areas of the tissue where analyte 201 density is medium a third color distinguishable from the first color and second color will be observed. In many cases it is possible for the microscopist to accurately estimate analyte 201 density levels based on the color of the stain. However, if more accurate measurements are required then the precise color of staining can be measured by image analysis.

Continuing the cytokeratin example from above, after step 104, the stained sample 200 may be analyzed under a microscope by a trained microscopist. The microscopist will note the colors present and will observe their distribution throughout the sample 200. The colors will range from a first color of yellow, in which the first chromogen 311 layer labels sites in the sample 200 having low analyte 201 density to a second color of blue in which the first chromogen 311 layer labels sites in the sample 200 having very high antigen density. Most of the sites will show a mixture of the first color yellow and the second color blue, which generates a third color green. The choice of chromogens is important since relatively few chromogens exhibit the desirable characteristics. Generally speaking the first chromogen 311 should yield a relatively light chromogen, yellow for example, and the second chromogen 321 should yield a dark chromogen, blue for example. The third color generated when these two chromogens are layered would be green. Thus the color distribution in this example would describe concentration density differentials of the analyte 201 in the sample 200 by labeling areas in the sample 200 with a range of color from yellow (low analyte density 402), to green (medium analyte density 403), to blue (high analyte density 404). Regions in the sample 200 that are not colored indicate regions of no analyte density 401. This color labeling may be used by the microscopist to estimate the relative analyte density in the sample 200 by the color distribution within the stained sample 200 as each color describes a different analyte 201 density in the biological sample 200.

Optionally, in order to achieve a more precise measure of analyte 201 density, image analysis could be used. First digital images are captured from the stained samples 200. Next the digital image is subjected to image analysis which analyzes the colored components of the digital image. For example in one method each pixel can be measured for red, green, and blue (RGB) values, or each pixel can be measured by another method for hue, saturation, and intensity. These measurements are then converted to analyte 201 density levels which may be magnitudes of orders greater than single color chromogen staining methods which typically use a typically use a range of 0-255 since color measurements can use scales up to several million.

As another example the method 100 may be used for labeling concentration density differentials of the analyte 201 Her2/neu in a biological sample. Human Epidermal Growth Factor Receptor-2 (HER2/neu) is a protein that is associated with certain types of breast cancer. The presence or absence of Her2/neu is critical for correct diagnosis and treatment. Even in cases where Her2/neu is present it is critical to estimate Her2/neu density as this also effects therapy decisions, so in this case we have a situation where both the presence or absence as well as the amount of Her2/neu is important for correct diagnosis and treatment.

A tissue biopsy may be obtained from a patient having breast cancer. A biological sample may be obtained from the biopsy which may be prepared for examination by fixation, embedding, sectioning, deparaffinization, rehydration, and target retrieval.

The method 100 may begin 101, and an enzyme marker 204 capable of acting on at least two chromogens (substrate/chromogens) may be bound to the Her2/neu analyte 201 contained in the biological sample 200 in step 102 by incubating the sample 200 with Her2/neu antibody for 20 minutes, rinsing, incubating the sample 200 with a linker antibody labeled with HRP for 20 minutes, and rinsing.

Next, the sample 200 may be incubated with a first chromogen 311 (substrate/chromogen) of HRP-Yellow for a first time period of five minutes to generate a first color chromogen-enzyme product 315 that is accumulated in the biological sample 200 at the binding site of the analyte 201 in step 103. In some embodiments, the first color chromogen-enzyme product 315 may be observable as a first color of yellow if Her2/neu is present. In other embodiments, the first color chromogen-enzyme product 315 may reflect light observable as a first color of yellow if Her2/neu is present. The sample 200 may then be rinsed.

Next, the sample 200 may be incubated with a second chromogen 321 (substrate/chromogen) of HRP-blue for a second time period of five minutes to generate a second color chromogen-enzyme product 325 that is accumulated in the biological sample 200 at the binding site of the analyte 201 in step 104. In some embodiments, the second color chromogen-enzyme product 325 may be observable as a second color of blue if Her2/neu is present. In other embodiments, the second color chromogen-enzyme product 325 may reflect light observable as a second color of blue if Her2/neu is present.

The sample 200 may be examined for the presence of the first color yellow or light observable as the first color yellow (low Her2/neu expression or concentration density), the presence of the second color blue or light observable as the second color blue (high Her2/neu expression), and the presence of a third color green or light observable as a third color green (moderate Her2/neu expression or concentration density). A combination of the light observable as the first color yellow and the light observable as the second color blue is observable as a third color green, thereby each color may describe a different analyte 201 density in the biological sample 200. Similarly, a combination of the first color chromogen-enzyme product 315 and second color chromogen-enzyme product 325 are observable as a third color green, thereby the first color describes a first analyte 201 density, the second color describes a second analyte 201 density, and the third color describes a third analyte 201 density.

The following Table shows a comparison between the scoring method for the standard Her2/neu IHC test and the Her2/neu method for labeling concentration density differentials of an analyte 201 in a biological sample 100 utilizing chromogen layering. The standard single stain method provides subjective results which usually must be analyzed with image analysis software, while the present method 100 layers two chromogens to provide definitive results which do not need to be analyzed with image analysis software.

TABLE 1

Comparison of Standard IHC to Chromogen Layering for determination of Her2/neu Levels.

| Standard IHC | Chromogen Layering IHC | Significance |
| --- | --- | --- |
| No staining, 0 | No staining | Her2/neu negative |
| Weak staining, 1+ | Yellow | Treatment not indicated |
| Moderate staining, 2+ | Green | Treatment indicated |
| Strong staining, 3+ | Blue | Treatment indicated |

The availability of multiple different colored chromogens is exploited by the method 100 via chromogen layering. A first chromogen 311 layer is applied that stains the tissue a first color. Next a second chromogen 321 is applied that stains the tissue a second color. By layering a second chromogen 321 on top of a first chromogen 311, a third color is generated that is distinct from either of the first two colors. Using two different colored chromogens to stain analytes 201 in a biological sample 200 created the unexpected results of the generation of a third color. While differential staining techniques exist, they are directed to staining different analytes 201 different colors. For example, Gram staining uses two dyes: Crystal violet and Fuchsin or Safranin (the counterstain) to differentiate between Gram-positive bacteria (large Peptidoglycan layer on outer surface of cell) and Gram-negative bacteria. The expected results from using two different chromogens to stain a single analyte 201 is that the two stains would obscure each other which is why using two different chromogens is commonly discouraged. We have discovered a novel method for labeling concentration density differentials of an analyte 201 in a biological sample 100 in which the distribution of the first, second, and third colors over the tissue is directly proportional to analyte 201 density in the tissue. Thus we have discovered a useful and easy method to estimate analyte 201 density in a tissue.

The explanation for this unexpected finding is as follows. Where analyte 201 density is scarce relatively few enzyme marker 204 molecules are bound. Whereas where antigen density is dense relatively more enzyme marker 204 molecules are bound. When the bound enzymes react with a first chromogen 311, a first color is generated at the binding site. As the react proceeds more color is generated while at the same time the enzyme marker 204 molecules become depleted. When the enzymes are completely depleted the reaction stops. At sites of low enzyme marker 204 binding the enzymes become nearly, or completely, depleted during the first chromogen 311 reaction. At sites where enzyme marker 204 binding is relatively higher, not all of the enzyme is depleted during the first chromogen 311 reaction, and sufficient enzyme remains for a subsequent reaction. When the second chromogen 321 is applied no color is generated at sites of enzyme depletion thereby remaining colored by the first chromogen 311 only. Whereas at sites containing active enzyme marker 204 a second color is generated that now deposits on top of the first color, and creates a third distinct color, thereby giving a differential color pattern to the sample 200 that is proportional to analyte 201 density.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A method for labeling concentration density differentials of a first analyte in a biological sample, the biological sample comprising a plurality of first analytes, the method including the steps of:
   a. binding a first target antibody linked to a first enzyme to the first analyte contained in a sample, the first enzyme capable of acting on at least two chromogens while bound to the first analyte;
   b. incubating the sample with a first chromogen for a first time period to generate a first color chromogen-enzyme product after the first enzyme reacts with the first chromogen while the first target antibody is bound to the first analyte, the first color chromogen-enzyme product reflecting light observable as a first color; and
   c. incubating the sample with a second chromogen while the first color chromogen-enzyme product is still present and the first enzyme has not been de-natured to generate a second color chromogen-enzyme product while the first target antibody is bound to the first analyte, the second color chromogen-enzyme product reflecting light observable as second color, and
   d. wherein a combination of the light observable as the first color and the light observable as the second color is observable as a third color while the first target antibody linked to the first enzyme is bound to the first analyte and the first enzyme has reacted with both the first color chromogen and the second color chromogen, and
   e. wherein the presences or absence of each of the first color, the second color, and the third color is useful to determine analyte density in the biological sample.

2. The method of claim 1, wherein the analyte density described by the second color is greater than the analyte density described by the first color, and wherein the analyte density described by the second color is greater than the analyte density described by the third color.

3. The method of claim 1, wherein the analyte density described by the third color is less than the analyte density described by the second color, and wherein the analyte density described by the second color is greater than the analyte density described by the first color.

4. The method of claim 1, wherein the first analyte is a protein selected from the group consisting of Human Epidermal Growth Factor Receptor-2 (HER2/neu), Programmed death-ligand 1, Anaplastic lymphoma kinase, epidermal growth factor receptor (EGFR), Receptor tyrosine-protein kinase, cytokeratin protein, and Mast/stem cell growth factor receptor.

5. The method of claim 1, wherein the first analyte is a nucleotide sequence of a nucleic acid used in the synthesis of a protein selected from the group consisting of Human Epidermal Growth Factor Receptor-2 (HER2/neu), Programmed death-ligand 1, Anaplastic lymphoma kinase, epidermal growth factor receptor (EGFR), Receptor tyrosine-protein kinase, cytokeratin protein, and Mast/stem cell growth factor receptor.

6. The method of claim 1, wherein the first color chromogen-enzyme product is observable as the color yellow, wherein the second color chromogen-enzyme product is observable as the color blue, and wherein the third color is observable as the color green.

7. The method of claim 1, wherein the first color chromogen-enzyme product is observable as the color red, wherein the second color chromogen-enzyme product is observable as the color blue, and wherein the third color is observable as the color purple.

8. The method of claim 1, wherein the first enzyme is Horseradish Peroxidase, and wherein at least one of the chromogens is selected from the group consisting of Diaminobenzidine (DAB), Aminoethylcarbazole (AEC), tetramethylbenzidine (TMB), 4-Chloronaphthol (4CN)), 4CN+p-phenylenediamine, Benzidine, and Phenylenediamine.

9. The method of claim 1, wherein the first enzyme is Alkaline Phosphatase, and wherein at least one of the chromogens is selected from the group consisting of: Naphthol Phosphate plus Fast Red, Naphthol Phosphate plus Fast Blue, Bromo chloro indoxyl phosphate (BCIP), and Chloro indoxyl phosphate (CIP).

10. The method of claim 1, wherein the first color chromogen-enzyme product is a precipitating dye, and wherein the second color chromogen-enzyme product is a precipitating dye.

11. A method for labeling concentration density differentials of a single analyte of a plurality of analytes in a biological sample, the method including the steps of:
   a. binding a first enzyme to the single analyte contained in a sample, the first enzyme capable of acting on at least two chromogens while bound to the single analyte;
   b. incubating the sample with a first chromogen for a first time period, allowing the first chromogen to bind to the first enzyme to generate a first color chromogen-enzyme product that is accumulated in the biological sample at the binding site of the single analyte, the first color chromogen-enzyme product observable as a first color; and
   c. incubating the sample with a second chromogen after the first enzyme has reacted with the first chromogen, allowing the second chromogen to hind to the first enzyme to generate a second color chromogen-enzyme product that is accumulated in the biological sample at the binding site of the single analyte, the second color chromogen-enzyme product observable as a second color, and
   d. wherein a combination of the first color chromogen-enzyme product and second color chromogen-enzyme product are observable as a third color, and
   e. wherein the first color describes a first analyte density, the second color describes a second analyte density, and the third color describes a third analyte density and wherein the first enzyme selectively binds to both the first chromogen and the second chromogen without being denatured at the site of the single analyte.

12. The method of claim 11, wherein the second analyte density is greater than the first analyte density, and wherein the second analyte density is greater than the third analyte density.

13. The method of claim 11, wherein the third analyte density is less than the second analyte density, and wherein the second analyte density is greater than the first analyte density.

14. The method of claim 11, wherein the single analyte is a protein selected from the group consisting of Human Epidermal Growth Factor Receptor-2 (HER2/neu), Programmed death-ligand 1, Anaplastic lymphoma kinase, epidermal growth factor receptor (EGFR), Receptor tyrosine-protein kinase, cytokeratin protein, and Mast/stem cell growth factor receptor.

15. The method of claim 11, wherein the single analyte is a nucleotide sequence of a nucleic acid used in the synthesis of a protein selected from the group consisting of Human Epidermal Growth Factor Receptor-2 (HER2/neu), Programmed death-ligand 1, Anaplastic lymphoma kinase, epidermal growth factor receptor (EGFR), Receptor tyrosine-protein kinase, cytokeratin protein, and Mast/stem cell growth factor receptor.

16. The method of claim 11, wherein the first color chromogen-enzyme product is observable as the color yellow, wherein the second color chromogen-enzyme product is observable as the color blue, and wherein the third color is observable as the color green.

17. The method of claim 11, wherein the first color chromogen-enzyme product is observable as the color red, wherein the second color chromogen-enzyme product is observable as the color blue, and wherein the third color is observable as the color purple.

18. The method of claim 11, wherein the first enzyme is Horseradish Peroxidase, and wherein at least one of the chromogens is selected from the group consisting of Diaminobenzidine (DAB), Aminoethylcarbazole (AEC), tetramethylbenzidine (TMB), 4-Chloronaphthol (4CN)), 4CN+p-phenylenediamine, Benzidine, and Phenylenediamine.

19. The method of claim 11, wherein the first enzyme is Alkaline Phosphatase, and wherein at least one of the chromogens is selected from the group consisting of: Naphthol Phosphate plus Fast Red, Naphthol Phosphate plus Fast Blue, Bromo chloro indoxyl phosphate (BCIP), and Chloro indoxyl phosphate (CIP).

20. The method of claim 11, wherein the first color chromogen-enzyme product is a precipitating dye, and wherein the second color chromogen-enzyme product is a precipitating dye.

* * * * *